United States Patent
Gutermuth et al.

(10) Patent No.: US 10,029,976 B2
(45) Date of Patent: Jul. 24, 2018

(54) PROCESS AND PLANT FOR THE PURIFICATION OF ACRYLIC ACID

(71) Applicant: L'Air Liquide, Societe Anonyme pour l'Etude et l'Exploitation des Procedes Georges Claude, Paris (FR)

(72) Inventors: Thomas Gutermuth, Maintal (DE); Markus Kreich, Otzberg (DE); Frank Castillo-Welter, Friedrichsdorf (DE)

(73) Assignee: L'Air Liquide Societe Anonyme Pour L'Etude Et L'Exploitation Des Procedes Georges Claude, Paris (FR)

( * ) Notice: Subject to any disclaimer, the term of this patent is extended or adjusted under 35 U.S.C. 154(b) by 0 days.

(21) Appl. No.: 15/317,755

(22) PCT Filed: Jun. 16, 2015

(86) PCT No.: PCT/EP2015/025033
§ 371 (c)(1),
(2) Date: Dec. 9, 2016

(87) PCT Pub. No.: WO2015/197197
PCT Pub. Date: Dec. 30, 2015

(65) Prior Publication Data
US 2017/0113994 A1  Apr. 27, 2017

(30) Foreign Application Priority Data
Jun. 26, 2014 (DE) .......... 10 2014 108 980

(51) Int. Cl.
C07C 51/48 (2006.01)
C07C 51/44 (2006.01)
(Continued)

(52) U.S. Cl.
CPC .............. *C07C 51/48* (2013.01); *B01D 3/143* (2013.01); *B01D 11/0488* (2013.01); *B01D 11/0492* (2013.01); *C07C 51/44* (2013.01)

(58) Field of Classification Search
CPC ......... C07C 51/48; C07C 51/44; B01D 3/143; B01D 11/0488; B01D 11/0492
See application file for complete search history.

(56) References Cited

U.S. PATENT DOCUMENTS

| | | | | |
|---|---|---|---|---|
| 3,798,264 A * | 3/1974 | Kubota et al. | .......... | C07C 51/48 203/15 |
| 3,859,175 A * | 1/1975 | Ohrui | .............. | C07C 51/46 203/46 |
| 6,737,546 B2 * | 5/2004 | Wagner | .......... | C07C 51/44 562/545 |

FOREIGN PATENT DOCUMENTS

| | | |
|---|---|---|
| DE | 102 51 328 | 6/2003 |
| FR | 2 119 764 | 8/1972 |

(Continued)

OTHER PUBLICATIONS

International Search Report and Written Opinion for PCT/EP2015/025033, dated Oct. 9, 2015.

*Primary Examiner* — Yate' K Cutliff
(74) *Attorney, Agent, or Firm* — Justin K. Murray (57) ABSTRACT

This invention relates to a process for the purification of acrylic acid from a mixture containing acrylic acid and acetic acid, comprising the following steps: extraction of the mixture containing acrylic acid and acetic acid with an extractant stream, whereby a raffinate stream and an extract stream are obtained, distillation of the extract stream, whereby an acrylic acid stream and a return stream are obtained, wherein the return stream contains acetic acid and is recirculated into the extraction.

(Continued)

Furthermore, the invention may include a plant for carrying out this process.

8 Claims, 4 Drawing Sheets

(51) Int. Cl.
    *B01D 3/14*        (2006.01)
    *B01D 11/04*      (2006.01)

(56) References Cited

FOREIGN PATENT DOCUMENTS

| FR | 2 162 486 | 7/1973 |
|----|-----------|--------|
| WO | WO 03/057656 | 7/2003 |

* cited by examiner

Fig. 4

PROCESS AND PLANT FOR THE PURIFICATION OF ACRYLIC ACID

CROSS REFERENCE TO RELATED APPLICATIONS

This application is a § 371 of International PCT Application PCT/EP2015/025033, filed Jun. 16, 2015, which claims the benefit of DE 10 2014 108 980.4, filed Jun. 26, 2014, both of which are herein incorporated by reference in their entireties.

FIELD OF THE INVENTION

This invention relates to a process for the purification of acrylic acid from a mixture containing acrylic acid and acetic acid.

BACKGROUND

With a global annual production of more than 4 mio. t, acrylic acid is one of the most produced intermediate products of the chemical industry, as acrylic acid and its derivatives are starting substances for numerous industrial-scale products. Particularly important are the so-called superabsorbents, to which acrylic acid is polymerized together with sodium acrylate (the sodium salt of acrylic acid). The same for the most part are employed in hygiene products (e.g. diapers), but are also used for the storage of water in soils. The esters of acrylic acid are converted to polymers, and the resulting plastics are used in paints or as dispersing agents.

Acrylic acid is industrially produced in a two-stage, heterogeneously catalyzed process. Proceeding from propene, acrolein is obtained at about 350° C. on bismuth molybdates with a selectivity and yield greater than 90 wt-%. In the second step, acrolein is oxidized further on mixed Mo/V/W oxides at about 280° C. to obtain acrylic acid. As by-products the total oxidation products CO, $CO_2$ and water are obtained as well as small amounts of acetic acid from the acetaldehyde obtained during the propene oxidation. Therefore, a multistage processing is carried out subsequent to the reaction.

A particular challenge in the purification of the acrylic acid is the polymerization tendency of the acrylic acid, in particular at elevated temperatures. The polymerization of acrylic acid is a strongly exothermal reaction which releases large amounts of heat. Since the heat in turn leads to an acceleration of the polymerization, acrylic acid tends to explosion-like polymerizations. A polymerization of acrylic acid often leads to clogging and thus to undesired shut-down periods of the entire plant. In this connection, the acetic acid obtained as by-product is to be classified as particularly problematic, as the same promotes the polymerization of acrylic acid as a proton donor.

DE 102 51 328 B4 describes a purification for acrylic acid in which the acetic acid is separated such that it can be obtained from the process in an economically exploitable manner. For this purpose, the reaction products from a mixture of cyclohexane and propyl acetate are absorbed in an extraction column and supplied to a solvent separation column. Cyclohexane is separated therein as top stream and after purification recirculated into the extraction column. The product stream in the bottom of the solvent separation column contains propyl acetate, acetic acid and acrylic acid. This stream is supplied to an acrylic acid separation tower from which acrylic acid is discharged as relatively pure product. The remaining mixture of acetic acid and propyl acetate, which also contains fractions of acrylic acid, is separated in an acetic acid separation tower, where acetic acid is discharged as product and propyl acetate is supplied into the extraction column as solvent.

It was found out, however, that with this purification variant the undesired polymer formation and the fouling both in the acrylic acid separation tower and in the solvent separation column occur to a considerable extent due to the relatively high concentration of the acetic acid. As a result, cloggings already occur within the plant after few weeks of operating time, which is why an intensive cleaning above all within the distillation columns and the associated heat exchangers becomes necessary with corresponding shut-down periods of the plant.

The acetic acid produced thereby has a comparatively high purity of >90 wt-%, but the relatively low sales revenue from the additional production of the acetic acid hardly or only with difficulty makes up for the expenditures for additional investments (e.g. in distillation columns, tank farms, loading etc.) as well as operative costs (e.g. increased consumption of resources). Furthermore, the increased polymer formation and fouling tendency results in distinct reductions in the availability of the plant as well as in acrylic acid product losses due to polymer formation and in additional costs for the disposal of the wastes which are obtained in the cleaning and removal of polymers.

With the catalysts commonly used today and the available reactor sizes, about 400 kg/h of acetic acid are produced in an acrylic acid plant as side reaction. A sales revenue of about 200,000 € (at a price of 500 €/t) can be achieved therewith. This revenue however is relativized by the acrylic acid losses connected with the separation of the acetic acid. On an assumption of an acrylic acid price of 1500 €/t, the revenue already is used up with losses of 130 kg/h of acrylic acid. Acrylic acid nowadays also achieves far higher market prices, and further costs, already described above, for additional investments as well as disposal costs have not yet been taken into account.

A process for the purification of acrylic acid by avoiding a polymer formation and a fouling within the plant is proposed in U.S. Pat. No. 3,798,264. Initially, reaction products are separated as condensate in a condenser and separated from low boilers in a stripping column. The remaining phase containing acrylic acid is separated from the aqueous phase in an extraction column by an extracting agent, wherein a part of the acetic acid already is removed with the aqueous phase. Subsequently, the extracting agent is separated from the acrylic acid and the acetic acid in a solvent separation column. Finally, the acetic acid is removed from the acrylic acid by distillation in an acrylic acid/acetic acid separation column, wherein the acetic acid obtained is supplied to the condensate, the stripping column or the extraction column. To avoid an acid-related polymerization within the acrylic acid/acetic acid separation column, a part of the acrylic acid is recirculated, whereby the acrylic acid concentration in the separation column is adjusted to values between 10 wt-% and 70 wt-%.

It has been noted, however, that the concentration of the acetic acid of 90 wt-% to 30 wt-% as described in the prior art cannot reliably prevent a polymer formation in the separation column and promotes fouling over an extended period. Furthermore, it is disadvantageous in the known processes that a part of the acrylic acid is recirculated not only within the separation column, but also back to the extractor. As a result, the acrylic acid repeatedly passes through the entire separating section including the distillation columns and thus is exposed to a thermal load for a comparatively long time, which in turn promotes the polymer formation and the fouling and at the same time leads to losses of the valuable product acrylic acid.

SUMMARY OF THE INVENTION

Therefore, it is the object of the present invention to provide a process and a plant for the purification of acrylic acid, wherein the disadvantages present in the prior art are overcome. In particular, it is intended to increase the availability (runtime/operating time) of the plant and to prevent a time- and cost-intensive cleaning of the distillation units, as this would also involve considerable production losses.

This object is solved by a process and a plant with the features of various embodiments described herein.

The process according to the invention for the purification of acrylic acid from a mixture containing acrylic acid and acetic acid may include an extraction of the mixture containing acrylic acid and acetic acid, whereby a raffinate stream and an extract stream are obtained. This is followed by a preferably multistage distillation of the extract stream, whereby an acrylic acid stream and a return stream are obtained, with the latter being introduced into the extractant stream. The return stream furthermore guides the acetic acid contained in the extract stream back into the extractant stream.

According to certain embodiments of the invention, the return stream contains at least 90 wt-%, preferably >95 wt-% of the acetic acid contained in the extract stream. The acrylic acid thereby can be withdrawn with very high purity.

Thus, a direct distillative separation step of acrylic acid and acetic acid as described in the prior art no longer is necessary with the process according to the invention. A high concentration of the acetic acid, in particular with high acrylic acid fractions, thereby is avoided and an acid-related polymerization of the acrylic acid is inhibited. Correspondingly, this results in considerably longer runtimes of the plant. As compared to the prior art, in which usually after few weeks of operating time an intensive cleaning above all within the distillation columns and associated heat exchangers is necessary with corresponding shut-down periods, the process according to the invention can be carried out over very long operating times (more than one year) without corresponding shut-down periods.

It is favorable that the acetic acid chiefly, namely for more than 50 wt-%, preferably for more than 60 wt-%, based on the total amount of acetic acid introduced into the extraction, already is removed from the process with the raffinate stream. Total amount in the sense of the invention is understood to be that amount of acetic acid which results from the sum of those amounts of acetic acid which are introduced into the extraction on the one hand via the mixture containing acrylic acid and acetic acid and on the other hand via the return stream.

However, it is decisive above all that in the raffinate stream already a distinctly larger amount of acetic acid is removed from the process than the amount of acetic acid which has been recirculated into the extractor with the return stream. Based on the amount of acetic acid contained in the return stream over 40% more, preferably even over 50% more of acetic acid are removed from the process than has reached the extractor with the return stream (taking the amount contained in the return stream as 100%, an amount of acetic acid corresponding to >140% or >150% is discharged in the raffinate). It thereby is ensured that the concentration of the acetic acid in the extract stream and in the subsequent distillation is comparatively low. For example, at a total amount of about 1000 kg/h of acetic acid to the extractor (from feed stream+return stream) about 600 kg/h are removed with the raffinate, while only about 400 kg/h are contained in the return stream.

The fraction of acetic acid in the extract stream obtained in the extraction can be <2 wt-%, preferably <1 wt-% based on the entire extract stream.

The remaining acetic acid can be recirculated to the extractor with the return stream in small concentrations, typically with 3 to 7 wt-%, preferably 5 wt-%, based on the total mass flow of the return stream.

The acetic acid can separately be introduced into the extraction or be joined with the extractant stream, and the resulting mixture can be introduced into the extraction.

In a preferred aspect, the mixture containing acrylic acid and acetic acid is mixed with a liquid, preferably water, before the extraction. This is preferred in particular when the acrylic acid is produced in a two-stage catalytic gas phase oxidation of propene at temperatures of 200 to 400° C. The liquid acts as quenching medium for the hot gas mixture of the oxidation.

It has been found to be favorable as well to separate the raffinate stream by means of stripping into a stripping agent stream (bottom) and into a residual stream (recovery stream/top), wherein the acetic acid contained in the raffinate stream remains in the stripping agent stream (bottom product). As stripping agent, water preferably is used.

During stripping, the acetic acid almost completely, namely for at least 99 wt-%, preferably for 99.9 wt-% based on the total amount of acetic acid introduced into the stripping unit, hence also remains in the stripping agent stream and can be discharged from the process. It should be emphasized that almost the entire amount of acetic acid gets into the stripper with the raffinate stream and correspondingly is discharged via the bottom (stripping agent stream).

It is preferred particularly when the residual stream (recovery stream/top) from the stripping unit is supplied to the extractant stream, as due to stripping additional extracting agent can be recovered from the raffinate stream, wherein the extracting agent typically is contained in the raffinate stream at small fractions, namely at less than 3 wt-%, preferably 2 wt-% based on the raffinate stream.

In addition, it can be provided that the residual stream (recovery stream) is separated into a less dense and into a denser liquid phase, wherein the less dense phase is supplied to the extractant stream and the denser phase is supplied to the raffinate. The purity of the less dense phase recirculated to the extractant stream is increased. In addition, possibly contained acetic acid is removed from the residual stream and the concentration of the acetic acid is reduced within the following distillation of the extract stream.

In a preferred aspect, the extracting agent is a mixture of isopropyl acetate and cyclohexane. In particular, extracting agents consisting of 70-20 wt-% isopropyl acetate and 30 to 80 wt-% cyclohexane based on the total amount of extracting agent were found to be advantageous. However, for example diethyl ketone, methyl propyl ketone, propanal (acrolein), (meth)acrolein, isobutene, methyl-tent-butyl ether (MTBE) or mixtures thereof also can be used as extracting agents.

In a particularly preferred aspect of the process, cyclohexane is separated from the extract stream before the distillation of the extract stream. This simplifies the following distillation of the extract stream and leads to a better separation efficiency of the corresponding distillation column.

The subsequent distillation can be carried out with moderate temperatures of <110° C., preferably <100° C., particularly preferably <95° C., and at pressures of <0.4 bar, preferably <0.3 bar, particularly preferably <0.2 bar.

The distillation of the extract stream preferably can be carried out in two stages, wherein in the first distillation stage the acrylic acid stream is at least partly discharged and the remaining stream of the second stage is separated into a return stream and a recirculation stream, wherein the recirculation stream is completely recirculated into the first stage. As a result, the concentration of the acrylic acid in the first stage and the separation of the return stream in the second stage is carried out. Due to this spatial and technical division of the separation tasks, namely the separation of the acrylic acid and the separation of the return stream, on several distillation stages, the conditions in one stage can be optimized for the respective separation task. As a result, a particularly careful and efficient separation is achieved. In particular, both stages operate with the moderate temperatures of <110° C., preferably <100° C., particularly preferably <95° C., and pressures of <0.4 bar, preferably <0.3 bar, particularly preferably <0.2 bar.

In the preferred configuration with two distillation stages, the first stage preferably operates at a lower pressure than the second stage. This takes account of the higher acrylic acid concentration at the bottom of the first stage. For the second stage a slightly higher pressure is sufficient and expedient, in order to be able to efficiently condense the relatively low-boiling extracting agent at the top of the second stage at moderate cooling water temperatures.

The object underlying the invention also substantially can be solved by a plant with the features as described herein in that there is provided a plant for the purification of acrylic acid from a mixture containing acrylic acid and acetic acid, in particular for carrying out a process according to the embodiments disclosed herein. The plant according to certain embodiments of the invention can include an extraction column for the extraction of a mixture containing acrylic acid and acetic acid. Through a conduit, an extractant stream is supplied to the extraction column. In addition, a distillation column for the distillation of the extract stream and a return conduit are provided. According to certain embodiments of the invention, the distillation column is designed such that via the return conduit at least one return stream is guided, which contains at least 90 wt-% of the acetic acid contained in the extract stream.

This return conduit and/or the extractant conduit open(s) preferably at the bottom of the extraction. When the extractant conduit opens at the bottom of the extraction, a configuration of the plant in which the return conduit first opens into the extractant conduit is preferred particularly. Directly or indirectly feeding the return stream into the bottom of the extraction has the advantage that the acetic acid contained in the aqueous return stream would have to pass all internal fittings in the extraction column, in order to get into the withdrawn extract stream at the top. By internal fittings in the extraction column, preferably trays, particularly preferably more than 60 trays, quite particularly preferably more than 90 trays, such a high separation efficiency can be achieved that the acetic acid recirculated via the return stream practically is withdrawn completely and thus an accumulation of the acetic acid during the operation of the plant is prevented.

The recovery of acetic acid as by-product as described in the prior art is omitted and hence a special separation of acetic acid and extractant stream no longer is necessary. Therefore, an additional separation unit as described in the prior art can be omitted in principle, whereby the equipment expenditure is reduced.

In a preferred aspect, a raffinate stripper is provided, wherein the raffinate stripper for stripping the raffinate stream is designed such that a stripping agent stream (bottom) and a residual stream (recovery stream/top) is obtained, wherein a return conduit partly supplies the stripping agent stream to a heater, and that a return conduit recirculates the heated stripping agent stream into the raffinate stripper. The heater provides the amount of heat required for stripping. In general, a direct addition of fresh stripping agent, preferably steam, hence is omitted and larger amounts of waste water are avoided.

In a particularly preferred aspect, a conduit is provided which supplies the residual stream (recovery stream) to a phase separator, wherein the phase separator is designed such that the residual stream (recovery stream) is separated into a less dense and into a denser phase. Furthermore, the less dense phase is guided into the extractant stream via one conduit, and the denser phase is guided into the raffinate stripper via another conduit.

In a preferred aspect, two distillation columns are provided, wherein the first distillation column is designed such that via conduits a stream consisting of at least 95 wt-%, preferably >96.5 wt-% acrylic acid is withdrawn. Via further conduits, the top product from the first distillation column gets into the second distillation column, from which a stream is recirculated into the first column via a return conduit. With relatively little technical effort and under mild conditions, a very high purity of the withdrawn acrylic acid can be achieved thereby, as this interconnection of first column, second column and recirculation into the first column at least is just as good as three columns connected in series.

BRIEF DESCRIPTION OF THE DRAWINGS

Further features, advantages and possible applications of the invention can also be taken from the following description of the drawings and the exemplary embodiment. All features described and/or illustrated form the subject-matter of the invention per se or in any combination, independent of their inclusion in the claims or their back-reference.

DETAILED DESCRIPTION OF THE INVENTION

Figure 1:
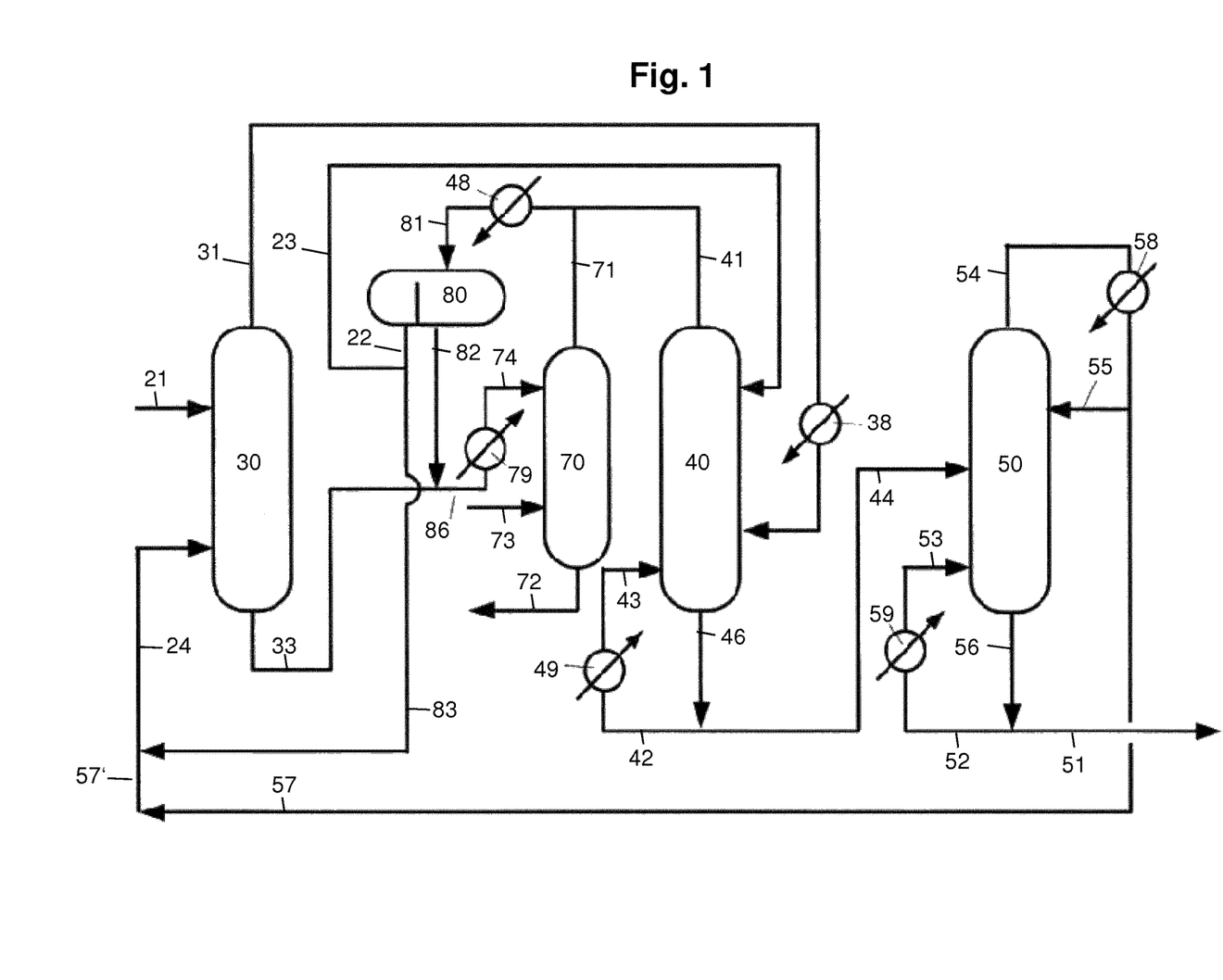
FIG. 1 shows a plant according to the invention with a distillation column and a raffinate stripper without heater.

The plant shown in FIG. 1 comprises an extraction column 30 for the extraction of a mixture containing acrylic acid and acetic acid, which is supplied to the extraction column 30 via conduit 21. Via conduit 24, an extractant stream, here a mixture of cyclohexane and isopropyl acetate, is supplied to the extraction column 30. Via conduit 33, the raffinate obtained from the extraction column 30 is passed into a stripper charge distributor 86, then into the heater 79 and via conduit 74 supplied to the raffinate stripper 70. The extract obtained in the extraction column 30 is introduced into a heat exchanger or heater 38 via conduit 31 and subsequently supplied to a solvent separation column 40.

A stripping agent, preferably steam, is supplied to the raffinate stripper 70 via conduit 73. Via conduit 72, a stripping agent stream is removed from the process. In this aspect of the invention, the main part of the acetic acid, namely >99 wt-% based on the raffinate stream, which introduces the main amount of acetic acid into the stripper 70, is discharged with the stripping agent stream. The residual stream obtained is discharged via conduit 71 and together with the top stream from conduit 41 of the solvent separation column 40 supplied to a heat exchanger 48. Via conduit 81, this unified stream is supplied from the heat exchanger 48 to a phase separator with 2 liquid phases, here a decanting drum 80.

The decanting drum 80 separates the residual stream coming from conduit 81 into a denser and a less dense liquid phase. The denser phase, which preferably represents an aqueous phase, is supplied to the stripper charge distributor 86 via conduit 82. The less dense phase, which preferably contains the extracting agent or parts thereof, is at least partly supplied via conduits 22 and 83 to the extractant stream in conduit 24. A part of the less dense phase also can be recirculated to the solvent separation column 40 via conduits 22 and 23.

In the present exemplary embodiment, the solvent separation column 40 is used for separating the cyclohexane from the extract stream. The cyclohexane is withdrawn as top stream via conduit 41, while the remaining extract stream, which here contains acrylic acid, isopropyl acetate and residual acetic acid, is supplied to a distillation column 50 via conduits 46, 44. A part of this residual extract stream also can be recirculated into the solvent separation column 40 via conduits 46, 42, 43 and in the process is heated in the heater 49.

From the distillation column 50 acrylic acid is removed from the process as acrylic acid stream via conduits 56, 51 as product with a purity of typically >95 wt-%, preferably >96.5 wt-%. A part of the acrylic acid stream also can be recirculated into the distillation column 50 via conduits 56, 52, 53 and in the process is heated in the heater 59. The return stream is withdrawn from the distillation column 50 via conduit 54 and contains acetic acid and isopropyl acetate. The return stream is condensed in the heat exchanger 58 and via conduit 57 supplied to the extractant stream in conduit 24. After the heat exchanger 58, a part of the extractant stream also can be recirculated to the distillation column 50 via conduit 55.

Figure 2:
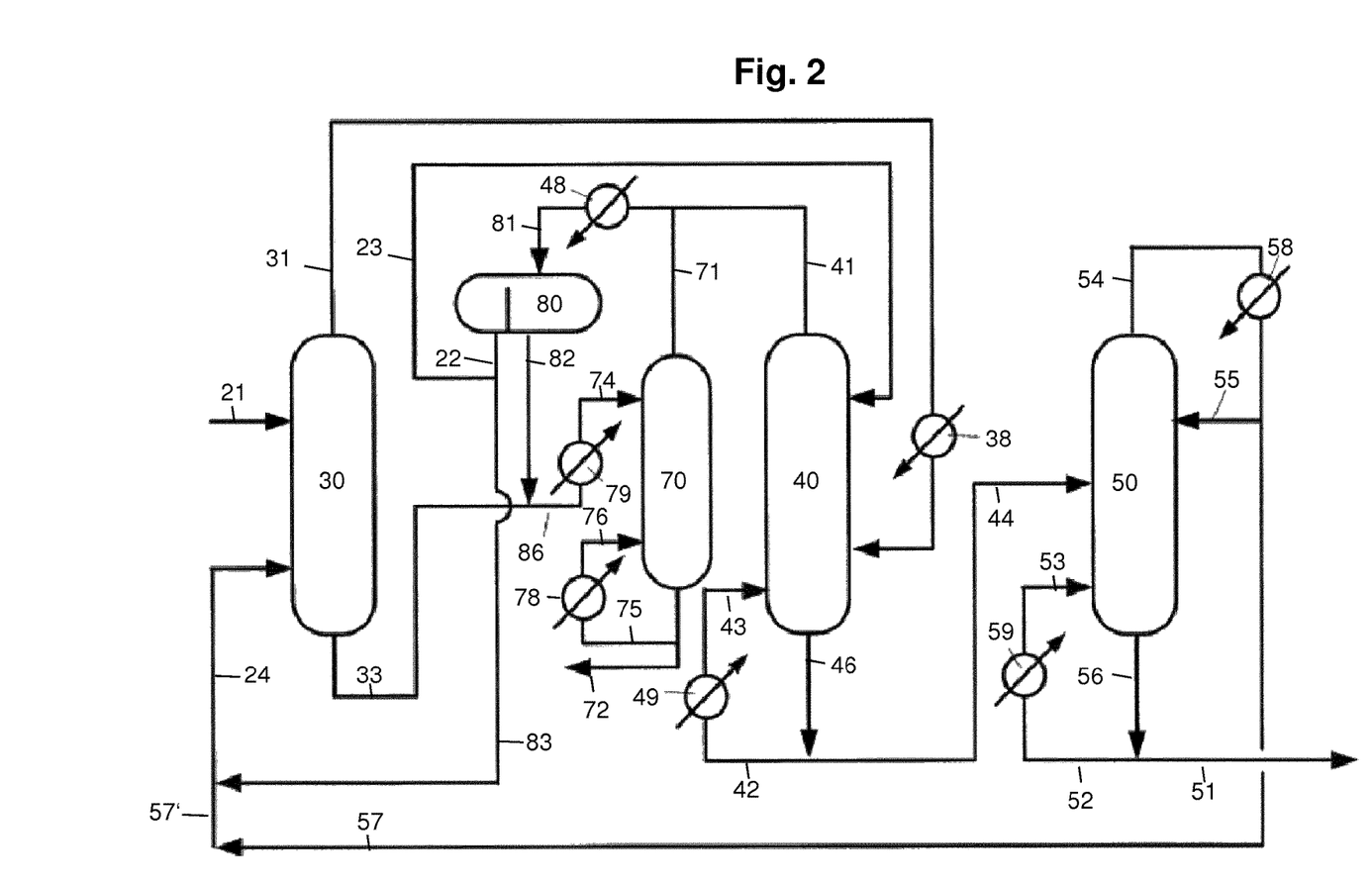
FIG. 2 shows a plant according to the invention as shown in FIG. 1 and a raffinate stripper with heater.
Figure 3:
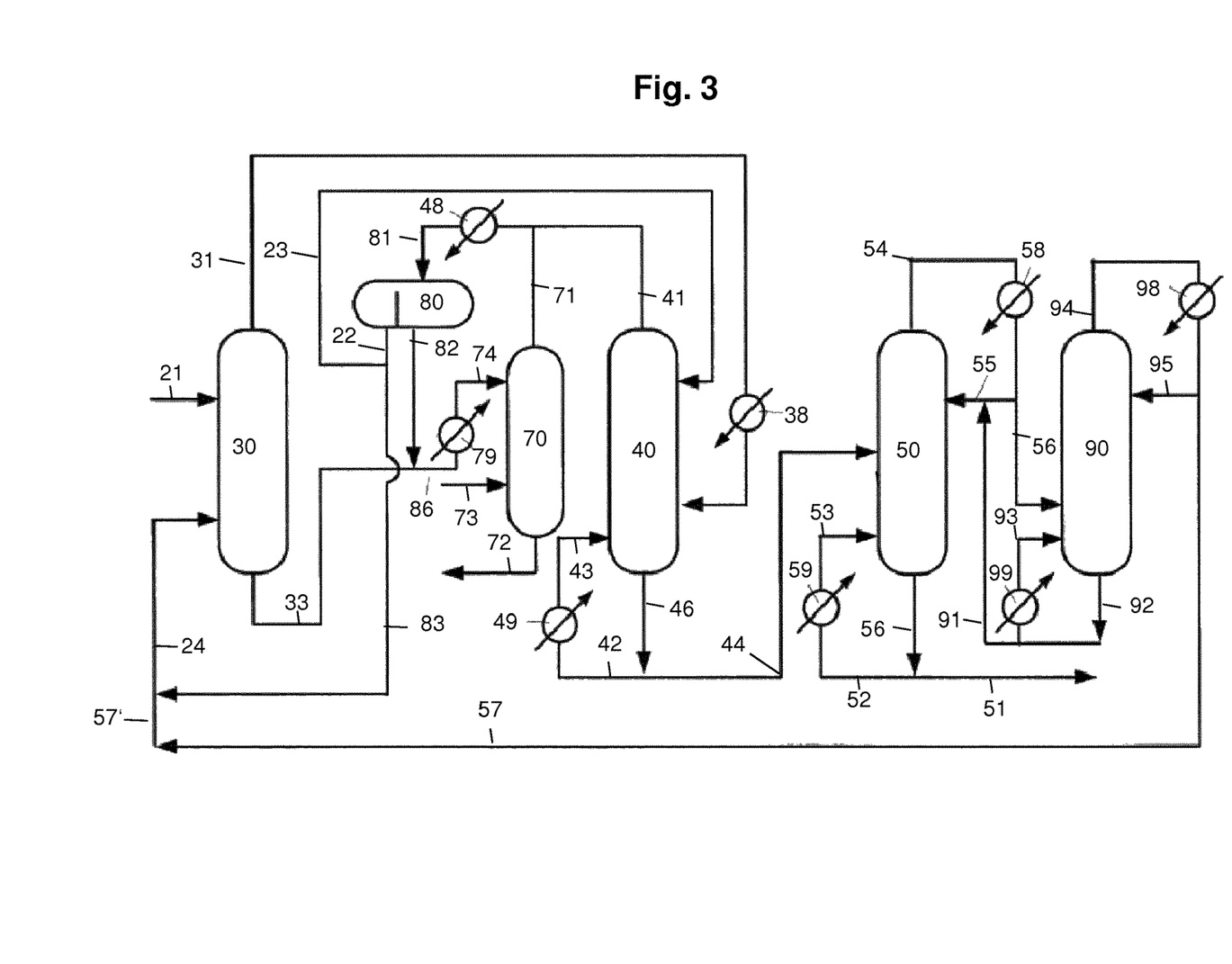
FIG. 3 shows a plant according to the invention with two distillation columns and a raffinate stripper without heater.

FIG. 2 shows a plant like that of FIG. 1. In addition, a part of the stripping agent stream is recirculated into the raffinate stripper 70 via conduits 75, 76 and in the process heated in the heater 78. A supply of fresh stripping agent via conduit 73, as shown in FIGS. 1 and 3, thereby can be omitted. The fraction of discharged stripping agent stream likewise is reduced, so that on the whole an ecologically and economically more efficient process is possible.

Figure 4:
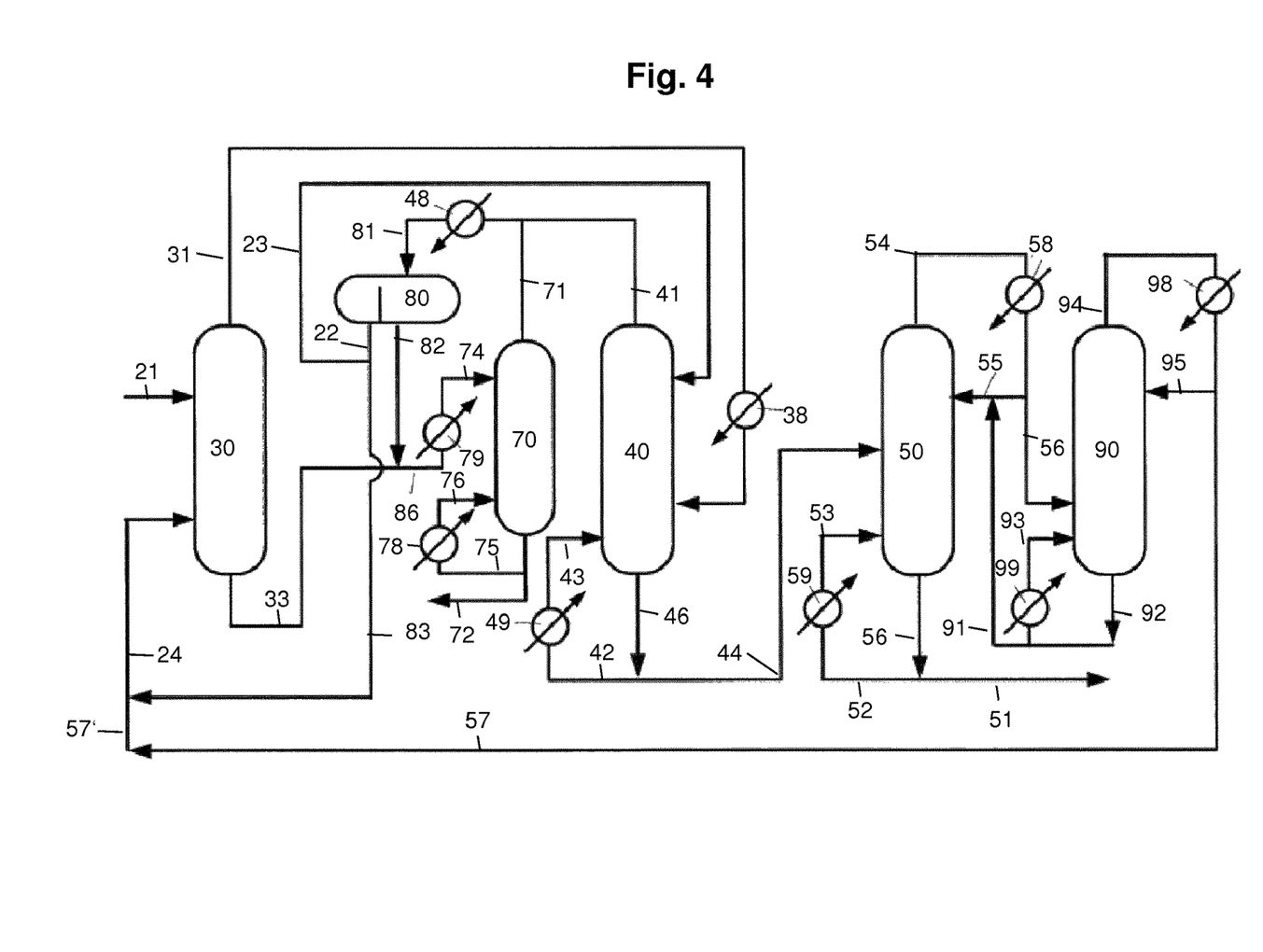
FIG. 4 shows a plant according to the invention as shown in FIG. 3 and a raffinate stripper with heater.

FIGS. 3 and 4 show a preferred aspect of the invention, wherein FIG. 3 in turn shows a raffinate stripper 70 without heater and FIG. 4 shows a raffinate stripper 70 with heater 78 and recirculation of the stripping agent stream via conduits 75, 76.

FIGS. 3 and 4 show a two-stage distillation of the extract stream, wherein the first stage corresponds to the distillation column 50 of FIGS. 1 and 2. In FIGS. 3 and 4, however, the return stream is not supplied directly via conduits 56, 57 to the extractant stream in conduit 24, but is first fed into a second distillation column 90 via conduit 56.

In the second distillation column 90, a recirculation stream is discharged via conduits 92, 91 and charged to the first distillation column 50 via conduit 55. A part of the recirculation stream can be introduced into the second distillation column 90 via conduits 92, 93 and in the process is heated by the heater 99. Via conduits 94, 57 and the heat exchanger 98, the return stream is introduced into the extractant stream in conduit 24. A part of this stream can be recirculated to the second distillation column 90 via conduit 95.

The following exemplary embodiment shows typical process conditions and concentrations in Table 1:

TABLE 1

| conduit | T/° C. | p/Mpa (a) | $c_{acrylic\,acid}$/ wt-% | $c_{acetic\,acid}$/ wt-% | $c_{cyclohexane}$/ wt-% | $c_{isopropyl\,acetate}$/ wt-% |
|---|---|---|---|---|---|---|
| 21 | 35 | 3 | 45-55 | — | — | — |
| 24 | 35 | 5 | <1 | <2 | 50-60 | 40-50 |
| 33 | 35 | 5 | <1 | <5 | — | <3 |
| 74 | 65 | 4 | <1 | <5 | — | <2 |
| 31 | 35 | 3 | 21 | <2 | 35-45 | 25-35 |
| 72 | 70 | 6 | <1 | <5 | — | — |
| 71 | 70 | <1 | — | <0.2 | <1 | 80-90 |
| 41 | | | | | | |
| 81 | | | | | | |
| 82 | 33 | 4 | — | — | <1 | <2 |
| 22 | 33 | 6 | — | — | 55-65 | 35-40 |
| 83 | 33 | 6 | — | — | 55-65 | 35-40 |
| 23 | 33 | 6 | — | — | 55-65 | 35-40 |
| 44 | 90-110 | 4 | 65-75 | <2 | <1 | 25-35 |
| 42 | 90-110 | 2 | 65-75 | <2 | <1 | 25-35 |
| 43 | 90-110 | 1 | 65-75 | <2 | <1 | 25-35 |
| 51 | 20 | 4 | >95 | — | — | — |
| 57 | 33 | 5 | <2 | <6 | <2 | 90-95 |

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a nonexclusive listing (i.e., anything else may be additionally included and remain within the scope of "comprising"). "Comprising" as used herein may be replaced by the more limited transitional terms "consisting essentially of" and "consisting of" unless otherwise indicated herein.

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value.

When such a range is expressed, it is to be understood that another embodiment is from the one particular value and/or to the other particular value, along with all combinations within said range.

All references identified herein are each hereby incorporated by reference into this application in their entireties, as well as for the specific information for which each is cited.

LIST OF REFERENCE NUMERALS 21-24 conduits
30 extraction column
31, 33 conduits
38 heater
40 solvent separation column
41-46 conduits
49 heater
48 heat exchanger
50 first distillation column
51-57 conduits
59 heater
58 heat exchanger
70 raffinate stripper
71-76 conduits
78 and 79 heater
80 decanting drum
81-83 conduits
86 stripper charge distributor
90 second distillation column
91-95 conduits
98 heat exchanger
99 heater

The invention claimed is:

1. A process for the purification of acrylic acid from a mixture containing acrylic acid and acetic acid, comprising the following steps:
   i) extracting the mixture containing acrylic acid and acetic acid with an extractant stream, whereby a raffinate stream and an extract stream are obtained; and
   ii) distilling the extract stream, whereby an acrylic acid stream and a return stream are obtained,
   wherein the return stream contains acetic acid and is recirculated into the extraction,
   wherein for the extraction a mixture of isopropyl acetate and cyclohexane is used as extracting agent,
   wherein before the distillation of the extract stream cyclohexane is separated from the extract stream.

2. The process as claimed in claim 1, wherein an absolute amount of acetic acid in the raffinate stream is greater than an absolute amount of acetic acid in the return stream.

3. The process as claimed in claim 1, wherein the return stream contains at least 90 wt-% of the acetic acid contained in the extract stream.

4. The process as claimed in claim 1, wherein before the extraction the mixture containing acrylic acid and acetic acid is mixed with a liquid.

5. The process as claimed in claim 1, wherein the raffinate stream is separated into a stripping agent stream and a residual stream by means of stripping, wherein the acetic acid contained in the raffinate stream remains in the stripping agent stream.

6. The process as claimed in claim 5, wherein the residual stream is supplied to the extractant stream.

7. The process as claimed in claim 6, wherein the residual stream is separated into a less dense and into a denser phase, wherein the less dense phase is supplied to the extractant stream and the denser phase is supplied to the raffinate stream.

8. The process as claimed in claim 1, wherein that the distillation of the extract stream is carried out in two stages, wherein in a first distillation stage the acrylic acid stream is at least partly discharged and a remaining stream of a second distillation stage is separated into a return stream and a recirculation stream, wherein the recirculation stream is completely recirculated into the first stage of the distillation.

* * * * *